United States Patent [19]

Antonini et al.

[11] 3,992,462

[45] Nov. 16, 1976

[54] 1,1,2,2-TETRACHLOROETHANE PREPARED BY OXYCHLORINATION OF DICHLOROETHYLENES

[75] Inventors: Albert Antonini, Paris; Claude Kaziz, La Courneuve; Georges Wetroff, Le Thillay, all of France

[73] Assignee: Produits Chimiques Pechiney-Saint-Gobain, Paris, France

[22] Filed: May 20, 1968

[21] Appl. No.: 730,651

[52] U.S. Cl. ............................................. 260/658 R
[51] Int. Cl.² ........................................ C07C 17/04
[58] Field of Search ............ 260/659, 662 A, 658 R

[56] References Cited
UNITED STATES PATENTS

| 2,399,488 | 4/1946 | Hearne | 260/659 D XY |
| 2,783,286 | 2/1957 | Reynolds | 260/659 D XY |
| 3,010,913 | 11/1961 | Price | 260/659 O XY X |
| 3,360,483 | 12/1967 | Diamond et al. | 260/659 D XY X |
| 3,427,359 | 2/1969 | Rectenwald et al. | 260/659 D XY |
| 3,461,084 | 8/1969 | Li | 260/659 D XY X |
| 3,468,968 | 9/1969 | Baker et al. | 260/659 D XY |

FOREIGN PATENTS OR APPLICATIONS 992,847  5/1965  United Kingdom ....... 260/659 OXY

OTHER PUBLICATIONS

Mantell, Adsorption, TP156, A35M3, 1951, c. 6.

*Primary Examiner*—Delbert E. Gantz
*Assistant Examiner*—Joseph A. Boska

[57] ABSTRACT

A process for preparation of 1,1,2,2-tetrachloroethane by oxychlorination of dichloroethylenes with a fluid bed catalyst with conversion of less than 70%.

19 Claims, No Drawings

1,1,2,2-TETRACHLOROETHANE PREPARED BY OXYCHLORINATION OF DICHLOROETHYLENES

This invention relates to the preparation of 1,1,2,2-tetrachloroethane by oxychlorination of cis-dichloroethylene and/or trans-dichloroethylene in a fluidized catalytic bed.

It is known that oxychlorination of dichloroethylenes, in the present of an appropriate catalyst, yields 1,1,2,2-tetrachloroethane. However, simultaneously with the production of 1,1,2,2-tetrachloroethane, side reactions occur such as dehydrochlorination reactions which yield $C_2$ unsaturated chlorinated compounds. It has been proposed to reduce the formation of $C_2$ unsaturated chlorinated compounds produced by diluting the reactants with hydrochloric acid. This method suffers from the drawback that increase in the volume of the reaction mass raises difficult problems of gas separation.

It is an object of this invention to provide a process which enables 1,1,2,2-tetrachloroethane to be obtained with very high selectivity and a high total conversion rate of dichloroethylenes while limiting the proportion of $C_2$ chlorinated ethylenic derivatives formed to less than 1 molar percent.

The object of this invention is achieved by a new combination which makes use with a fluidized bed catalyst of a well defined reaction zone temperature, a predetermined feed ratio of reactants (particularly that of oxygen to dichloroethylenes), a predetermined limitation of the percent conversion of dichloroethylenes into 1,1,2,2-tetrachloroethane, and recycling of separated dichloroethylenes which are not transformed, with the above conditions taken alone and preferably in combination.

Furthermore, the invention has for an object a catalytic system adapted for use in the process for the oxychlorination of dichloroethylenes.

An important concept of this invention resides in limitation of the oxychlorination reaction to a maximum of 70% total conversion of cis-dichloroethylene and/or trans-dichloroethylene. The untransformed cis-dichloroethylene and/or transdichloroethylene is separated from the reaction product and recycled in the system. Applicants have found that to obtain total conversion rates of the dichloroethylenes beyond 70%, it is necessary to raise the temperature and/or to increase the residence time of the materials in the catalytic zone. This results in decrease of selectivity in 1,1,2,2-tetrachloroethane by formation of $C_2$ chlorinated ethylenic derivatives and by formation of combustion by-products and/or decrease in productivity of the described process.

In accordance with the oxychlorination of this invention, cis-dichloroethylene and/or trans-dichloroethylene, hydrochloric acid and a gas containing molecular oxygen are passed at a temperature within the range of 200° to 360° C, and preferably 200° to 320° C through a catalytic zone which makes use of a fluidized bed catalyst, and in which the cis-trichloroethylene and/or trans-dichloroethylene is transformed at a conversion rate below 70% and preferably within the range of 40 to 70%. The 1,1,2,2-tetrachloroethane is separated from the reaction product, at least partially, and untransformed cis-dichloroethylene and trans-dichloroethylene are recycled to the feed.

In the event that use is made of an oxygen-containing gas which contains more than 20 molar percent gases that are inert to the reaction, such as $N_2$, $CO_2$ and CO, the untransformed dichloroethylenes are separated from the effluent from the catalytic reaction zone by well known means and preferably by cooling and then washing the effluent with an organic solvent, such as 1,1,2,2-tetrachloroethane, followed by distillation to separate the dissolved dichloroethylenes for recycling.

In accordance with a preferred practice of this invention, use is made of practically pure oxygen or pure as the molecular oxygen containing reactant. In such event, the 1,1,2,2-tetrachloroethane formed is partially or entirely separated from the effluent of the catalytic reaction zone by condensation with cooling, whereas the uncondensed gases which contain a part of the untransformed dichloroethylenes are recycled in quasi-totality. The other part of the untransformed dichloroethylenes which have condensed with the 1,1,2,2-tetrachloroethane is separated by distillation to enable re-use in the reaction.

Another factor is the rate of feed of the reactants. The feed flow rate is based on the feed flow rate of the cis-dichloroethylene and/or trans-dichloroethylene which is maintained in the range of 0.5 to 20 moles per hour per liter of catalyst and preferably 2 to 8 moles per hour per liter of catalyst. The feed molar ratios of the reactants HCl/(cis CHCl = CHCl + trans CHCl = CHCl) is within the range of 0.8 to 2 and preferably 1.0 to 1.6 and $O_2$/(cis CHCl = CHCl + trans CHCl = CHCl) within the range of 0.2 to 0.6 and preferably 0.3 to 0.5.

According to an advantageous embodiment of this process, 1,1,2,2-tetrachloroethane is introduced as an added component to the feed of reactants to the catalytic reaction zone. When added to the feed, the 1,1,2,2-tetrachloroethane is employed in a molar ratio, with respect to the cis-dichloroethylene and/or trans-dichloroethylene, of less than 2.

The catalyst used for carrying out the process of the invention comprises a catalytic agent deposited on a carrier in which the carrier is formed of particles having a size within the range of 10 to 900 microns, presenting an average specific surface area above 1 $m^2/g$ and preferably above 10 $m^2/g$. The average particle size of the carrier is within the range of 20 to 400 microns and preferably 40 to 120 microns.

The term "average specific surface area" is used, owing to the fact that if a series of catalyst control samples are taken from different points of the catalytic bed for the purpose of determining the specific surface area of the carrier, in accordance with the B.E.T. method, the measurements show a dispersion in which the extreme values do not exceed the average value by more than 25%.

The carrier for the catalytic agent is formed of one or more substances of the type selected from the group comprising alumina, magnesia, graphite, activated carbon, aluminosilicates and preferably clays and silica having the aforementioned characteristics. Good results can be obtained with an attapulgite type clay which, when used in the oxychlorination reaction of this invention, prevents an average specific surface area ranging from 10 to 160 $m^2/g$. Very good results can be obtained with a carrier consisting essentially of silica and magnesia having an average specific surface area within the range of 40 to 200 $m^2/g$ and which exhibits excellent fluidization characteristics.

As the catalytic agents, use can be made of at least a compound of the following list of elements, namely: alkali metals, alkaline earth metals, bismuth, cadmium, chromium, cobalt, copper, tin, iron, magnesium, manganese, nickel, platinum, rare earths, thorium, vanadium, zinc and zirconium.

Particularly advantageous results are secured when the process of this invention is carried out under a pressure within the range of 1 to 10 absolute bars and preferably 2 to 8 absolute bars. Pressures higher than 10 absolute bars can be employed, the equipment permitting, but no marked advantage is derived from the use of such higher pressures.

The following examples are given by way of illustration, but not by way of limitation, of this invention:

EXAMPLE I

The oxychlorination reaction of a cis-dichloroethylene and trans-dichloroethylene mixture, containing 62 molar percent of the cis-compound and 38 molar percent of the trans-compound, is carried out in a glass reactor having an internal diameter of 65 mm and a height of 1000 mm and which is heated externally with electrical resistance heaters. The lower portion of the tube is formed with a reversed cone filled with 2 mm glass beads for mixing the reactants and diffusing the gases into the catalytic bed. The height of the catalytic bed, at rest, after fluidization, is 450 mm.

The catalyst is prepared by impregnating an attapulgite clay with an aqueous solution of $CuCl_2.2H_2O$ and KCl in an amount to provide a final content of dry catalyst in copper and potassium cations of 8.7 and 4.9% by weight respectively. The average specific surface area of the carrier, after the catalyst has been operated under normal running conditions for a hundred hours of reaction, is about 80 $m^2/g$. The catalytic mass presents a particle size ranging from 100 to 315 microns, 50% of which have a particle size below 210 microns.

During the operation, the reactants cis-dichloroethylene, trans-chloroethylene, air and gaseous hydrochloric acid are introduced under an absolute pressure of 1.05 bar at the lower portion of the reversed cone and the reactor is heated by the electrical resistance heaters controlled by thermocouples placed between the external wall of the tube and the electrical resistance heaters. The temperature of the fluid catalytic bed remains constant and uniform at 315° C ± 2° C. The feed flow rate in cis-dichloroethylene and trans-dichloroethylene is 2.37 moles per hour per liter of catalyst and the feed molar ratios of the reactants are:

HCl/(cis-CHCl = CHCl ± trans-CHCl = CHCl) = 1.35

$O_2$/(cis-CHCl = CHCl ± trans-CHCl = CHCl) = 0.37

The effluent from the catalytic reaction zone is cooled and washed with water in a washing column. The condensed organic layer is separated from the aqueous layer by continuous decantation and the separated organic layer is distilled to remove the 1,1,2,2-tetrachloroethane from the untransformed cis-dichloroethylene and trans-dichloroethylene. The gaseous products remaining after cooling and washing with water are stripped by countercurrent flow with 1,1,2,2-tetrachloroethane cooled to a temperature of 0° C in a washing column. The gases issuing from the column contain less than 0.5% cis- and trans-dichloroethylenes. The washing solution is distilled to separate the 1,1,2,2-tetrachloroethane from the dissolved cis- and trans-dichloroethylenes.

The entire amount of cis- and trans-dichloroethylenes is recovered, recycled to the feed of the reactor while a part of the separated 1,1,2,2,-tetrachloroethane is employed in the column for washing the gases, as previously described. The remainder is rectified as product.

The analysis of the effluent from the catalytic reaction zone shows that 62.2% of the mixture of cis- and trans-dichloroethylene is converted while 95.5% of the hydrochloric acid is converted.

The recovery of the untransformed cis- trans-dichloroethylenes is carried out with a yield of 98.7%. When the process is in normal continuous operation, the production of rectified 1,1,2,2-tetrachloroethane as product represents 97.3% of the cis- and trans-dichloroethylenes involved in the reaction.

1,1,2-trichloroethane is also obtained in an amount corresponding to 1.3% of the cis- and trans-dichloroethylenes involved and pentachloroethane represents 0.27% of the cis- and trans-dichloroethylenes involved. The combustion remains below 0.2% and the formation of trichloroethylene is about 0.5% of the cis- and trans-dichloroethylenes involved.

EXAMPLE II

The same reaction is carried out in a reactor similar to that of Example I but in which the internal diameter is 112 mm and which is equipped with a cooling system for the catalytic bed in the form of a stainless steel tube immersed in the bed and through which a heat exchange fluid is circulated at a temperature of 160° C. A catalyst identical to that of Example I is used and the height of the catalytic bed is 55 cm.

During the operation, the catalytic bed is maintained in a fluidized state at 308° ± 2° C and the reactor is fed under an absolute pressure of 1.1 bar with a mixture of vapors of cis- and trans-dichloroethylenes, hydrochloric acid and oxygen at a rate of 3.5 moles of cis- and trans-dichloroethylenes per hour per liter of catalyst in the molar ratio of cis-dichloroethylene to the total of cis- and trans-dichloroethylene of 57.8%.

The effluent from the catalytic reaction zone is cooled at 25° C to condense the major part of the 1,1,2,2-tetrachloroethane that is formed and which contains dissolved untransformed cis- and trans-dichloroethylenes and a very small amount of hydrochloric acid. The condensed effluent contains cis- and trans-dichloroethylenes, untransformed oxygen, untransformed hydrochloric acid, very small amounts of uncondensed 1,1,2,2-tetrachloroethane and traces of $CO_2$. A fraction, representing 5 volume percent, is separated out and washed with 1,1,2,2-tetrachloroethane in order to recover the dichloroethylenes contained therein while the remaining 95% is recycled and mixed with fresh reactants as feed. The condensed solvents and the washing solvents are distilled in order to separate out the cis- and trans-dichloroethylenes which are recycled to the feed and to purify the 1,1,2,2-tetrachloroethane as product.

After reaching normal running conditions, the reactor feed comprises:

|  | molar % |
|---|---|
| cis- and trans-dichloroethylenes | 35.6 |
| HCl | 47.8 |

|   | molar % |
|---|---|
| $O_2$ | 12.8 |
| 1,1,2,2-tetrachloroethane | 1.1 |
| $CO_2$ | 0.6 |
| $N_2$ | 1.8 |
| miscellaneous | 0.3 |

The analysis of the effluent from the catalytic reaction zone shows that the cis- and trans-dichloroethylenes are transformed at a rate of 55.9%.

The total yield of 1,1,2,2-tetrachloroethane is 97.6% with respect to the cis- and trans-dichloroethylenes involved. The formation of by-products is low, namely:

| 1,1,2-trichloroethane | 1.1 % of the cis- and trans-dichloroethylenes involved |
|---|---|
| pentachloroethane | 0.3 % of the cis- and trans-dichloroethylenes involved |

The combustion is less than 0.2% and the formation of trichloroethylene is less than 0.4% of the cis- and trans-dichloroethylenes involved.

The hydrochloric acid is used at a rate of 98.5% and oxygen at a rate of 98.7%.

It will be apparent from the foregoing that we have provided a new and improved process for the production of 1,1,2,2-tetrachloroethane in high yields and in a high state of purification by oxychlorination of cis- and trans-dichloroethylenes with a fluidized bed catalyst.

It will be understood that changes may be made in the details of formulation and operation without departing from the spirit of the invention, especially as defined in the following claims.

We claim:

1. A process for preparation of 1,1,2,2-tetrachloroethane containing less than 1 molar % chlorinated ethylenic compounds formed by oxychlorination of dichloroethylene selected from the group consisting of cis-dichloroethylene and trans-dichloroethylene and mixtures thereof, comprising the steps of passing a gaseous mixture of 1,2-dichloroethylene, hydrochloric acid and a molecular oxygen-containing gas wherein the ratio of HCl to dichloroethylene is within the range of 0.8 to 2.0 and the ratio of $O_2$ to dichloroethylene is within the range of 0.2 to 0.6 at a temperature within the range of 200° to 360° C through a catalytic reaction zone containing an oxychlorination catalyst deposited on a carrier having a specific surface area within the range of 10–200 m²/g in a fluidized state at a feed flow rate of the dichloroethylene of 0.5 to 20 moles per hour per liter of catalyst to effect less than 70% conversion of the dichloroethylenes fed to the reactor during passage through the catalytic reaction zone.

2. The process as claimed in claim 1 which includes the step of separating untransformed dichloroethylenes from the effluent of the catalytic reaction zone and recycling the separated untransformed dichloroethylenes to make up a part of the gaseous feed.

3. The process as claimed in claim 1 which includes the step of separating at least a part of the converted 1,1,2,2-tetrachloroethane from the effluent from the catalytic zone.

4. The process as claimed in claim 1 in which 40 to 70% of the dichloroethylenes is transformed during passage through the catalytic reaction zone.

5. The process as claimed in claim 1 in which the molecular oxygen containing gas is relatively pure oxygen.

6. The process as claimed in claim 1 in which the reaction is carried out at a temperature within the range of 200° to 320° C.

7. The process as claimed in claim 1 in which the gaseous reactants are passed through the catalytic reaction zone at a feed rate based upon the dichloroethylenes of 0.5 to 20 moles per hour per liter of catalyst.

8. The process as claimed in claim 1 in which the gaseous reactants are passed through the catalytic reaction zone at a feed rate based upon the dichloroethylenes of 2 to 8 moles per hour per liter of catalyst.

9. The process as claimed in claim 1 in which the molar feed ratio of hydrochloric acid to dichloroethylenes is within the range of 1.0 to 1.6.

10. The process as claimed in claim 1 in which the molar feed ratio of oxygen to dichloroethylenes is within the range of 0.3 to 0.5.

11. The process as claimed in claim 1 in which the gaseous reactants are passed into the catalytic reaction zone at a feed rate based upon dichloroethylenes within the range of 0.5 to 20 moles per hour per liter of catalyst and in which the reactants are present in the feed ratio of hydrochloric acid to dichloroethylenes within the range of 0.8 to 2.0 and oxygen to dichloroethylenes within the range of 0.2 to 0.6.

12. The process as claimed in claim 1 in which the gaseous reactants are passed through the catalytic reaction zone at a temperature within the range of 200° to 320° C. and at a feed rate based upon dichloroethylenes of 2 to 8 moles per hour per liter of catalyst and in which the reactants are present in the feed ratio of hydrochloric acid to dichloroethylenes within the range of 1.0 to 1.6 and oxygen to dichloroethylenes within the range of 0.3 to 0.5.

13. The process as claimed in claim 1 which includes the addition of 1,1,2,2-tetrachloroethane as a component of the gaseous feed mixture in the molar ratio, based upon the dichloroethylenes, of less than 2.

14. The process as claimed in claim 1 in which the carrier is of a size within the range of 10 to 900 microns.

15. The process as claimed in claim 1 in which the carrier is an attapulgite clay.

16. The process as claimed in claim 15 in which the attapulgite clay has an average specific surface area within the range of 10 to 160 m²/g.

17. The process as claimed in claim 1 in which the carrier consists of a mixture of magnesia and silica.

18. The process as claimed in claim 17 in which the magnesia and silica carrier has an average specific surface area within the range of 40 to 200 m²/g.

19. The process as claimed in claim 1 in which the oxychlorination reaction is carried out at a pressure within the range of 1 to 10 absolute bars.

* * * * *